United States Patent [19]

Boeck et al.

[11] Patent Number: 5,072,052

[45] Date of Patent: Dec. 10, 1991

[54] PROCESS FOR THE PRODUCTION OF ACROLEIN BY CATALYTIC GAS-PHASE OXIDATION OF PROPENE

[75] Inventors: Wolfgang Boeck, Langenselbold; Dietrich Arntz, Oberursel, both of Fed. Rep. of Germany; Guenter Prescher, Larchmont, N.Y.; Werner Burkhardt, Brachtal, Fed. Rep. of Germany

[73] Assignee: Degussa Aktiengesellschaft, Frankfurt am Main, Fed. Rep. of Germany

[21] Appl. No.: 581,696

[22] Filed: Sep. 12, 1990

[30] Foreign Application Priority Data

Sep. 13, 1989 [DE] Fed. Rep. of Germany ....... 3930534

[51] Int. Cl.$^5$ .............................................. C07C 45/34
[52] U.S. Cl. .................................. 568/479; 568/475; 568/476
[58] Field of Search ................. 568/475, 476, 479, 480

[56] References Cited

U.S. PATENT DOCUMENTS

| | | |
|---|---|---|
| 4,245,118 | 1/1981 | Yamamoto et al. ............... 568/476 |
| 4,267,385 | 5/1981 | Umemura et al. ................. 568/476 |
| 4,332,971 | 6/1982 | Dalton et al. ..................... 568/476 |
| 4,335,264 | 6/1982 | Yates et al. ........................ 568/476 |

FOREIGN PATENT DOCUMENTS

| | | |
|---|---|---|
| 0184790 | 6/1986 | European Pat. Off. ............ 568/479 |
| 0279374 | 2/1988 | European Pat. Off. ............ 568/479 |
| 3113179 | 1/1982 | Fed. Rep. of Germany ...... 568/479 |
| 3125061 | 3/1984 | Fed. Rep. of Germany ...... 568/479 |
| 3300044 | 1/1987 | Fed. Rep. of Germany ...... 568/479 |
| 3338380 | 10/1988 | Fed. Rep. of Germany ...... 568/479 |
| 2044764 | 10/1980 | United Kingdom ............... 568/479 |

Primary Examiner—Werren B. Lone
Attorney, Agent, or Firm—Beveridge, DeGrandi & Weilacher

[57] ABSTRACT

The present invention relates to a process for the production of acrolein by catalytic gas-phase oxidation of propene with air in the presence of steam and an inert gas or waste gas from the reaction, the starting materials being passed in defined quantitative ratios at 300° to 380° C. under 1.4 to 2.2 bar pressure over a catalyst containing the combination of elements MoFeCoNiBiP(As)K(Rb,Cs)SmSiO in the form of a bed of individual elements, the catalyst elements fulfilling certain geometric conditions and a number of critical physico-chemical parameters and a specific load of 2 to 8 mol propene/dm$^3$ catalyst bed/h being adjusted.

6 Claims, 2 Drawing Sheets

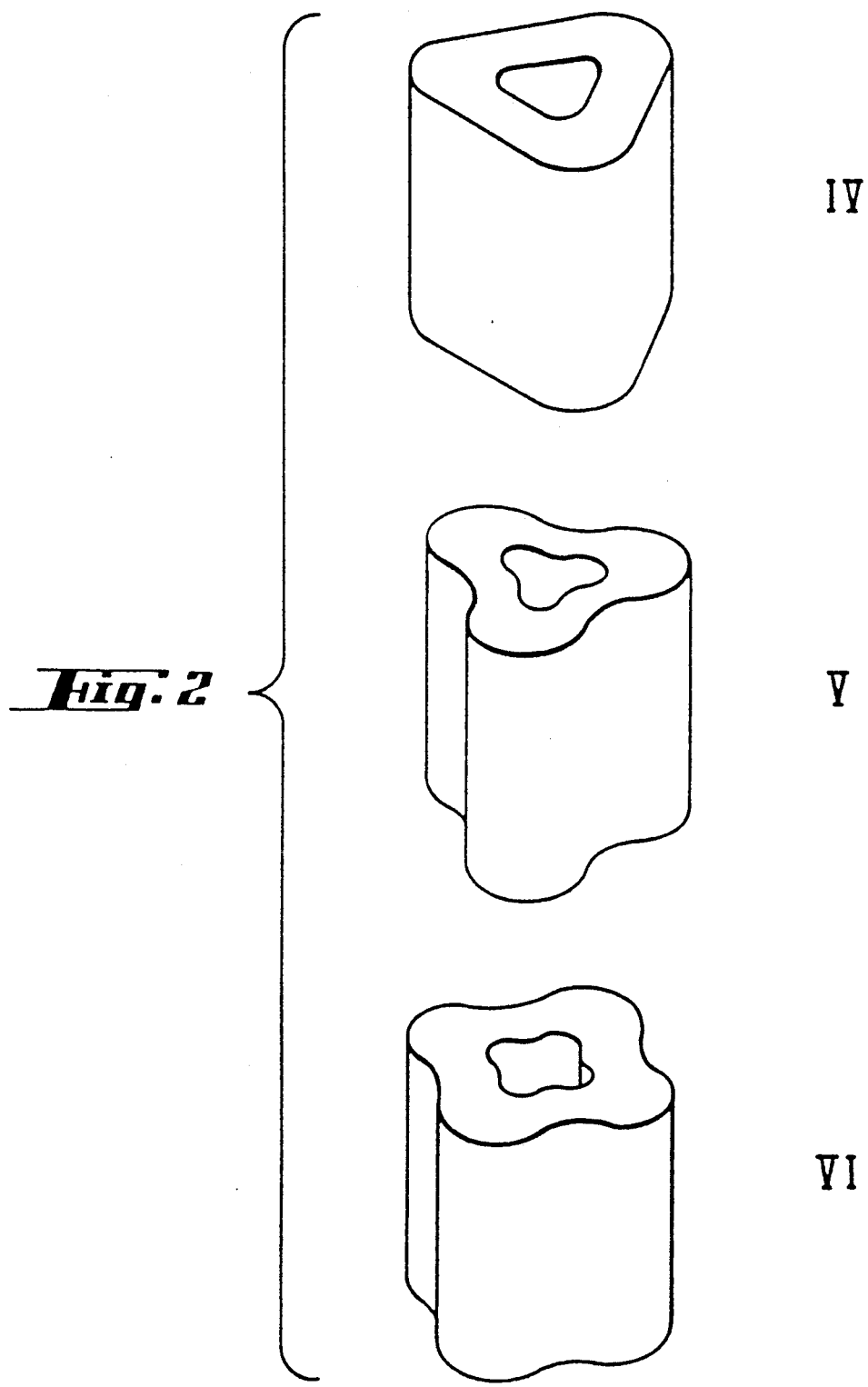

PROCESS FOR THE PRODUCTION OF ACROLEIN BY CATALYTIC GAS-PHASE OXIDATION OF PROPENE

BACKGROUND OF THE INVENTION

The present invention relates to a process for the production of acrolein by catalytic gas-phase oxidation of propene with air in the presence of steam and an inert gas or, preferably, waste gas from the reaction, from which the condensible constituents have been removed, at elevated temperature and in a ratio of propene to air to inert gas or waste gas to water of 1:6–9:3–12:0–5.

The highly exothermic reaction of propene on heterogeneous catalysts with an oxygen-containing gas leads to a number of unwanted secondary products in addition to the desired product acrolein. It is known that local overheating of the catalyst and the resulting increased formation of secondary products can be avoided by effective dissipation of the heat of reaction, for example in tube bundle reactors.

It is also known that the pressure loss of a catalyst bed can be influenced by the size and external shape of the catalyst elements. The internal structure of the catalyst elements (porosity, length of the diffusion paths) critically determines mass transfer and heat transfer in the catalyst and, accordingly, has a major bearing on selectivity along with the composition of the catalytically active mass. High compressive strength and abrasion resistance are requirements which a catalyst has to satisfy for use on an industrial scale. High abrasion would mean that, during filling of the tubes of a tube bundle reactor, the scattering of the pressure losses of the individual tubes would be high, resulting in different throughflow rates and impaired selectivity.

DE-PS 31 25 061 describes a process for the production of acrolein using shell catalysts. With shell catalysts, local overheating is avoided by the temperature-equalizing effect of the inert support; in the relatively thin shell, the diffusion paths for the gaseous reactants are short.

DE-OS 33 38 380 describes catalysts for the oxidation of propene to acrolein which are made in the form of rings or hollow cylinders from a mass containing Mo, Fe, Bi and W. These catalysts may be assumed to have been derived from shell catalysts by replacement of the inert core of the shell catalysts by an "inert void", the shell being open on two opposite sides to allow the reactants access to the void. Compared with shell catalysts, these ring or hollow cylinder catalysts have a larger ratio of outer surface to volume. The active mass is thus more accessible to the reactants. The low pressure loss and high heat dissipation of the shell catalysts are again present. To ensure that the "hollow catalysts" have sufficient mechanical strength, the active mass is highly compressed, with the result that the inner structure is adversely affected.

EP-OS 0 184 790 describes ring-shaped catalysts, albeit with rounded end faces to improve fillability, but does not mention either the catalyst mass or a special production process; in particular, there is no reference to measures for producing a special, favorable inner structure.

In order to enable the active mass to be optimally utilized, the inner structure of the catalyst has to be such that a potentially high reaction velocity is not limited by obstacles to mass transfer within the catalyst. An attempt along these lines is described in EP-OS 0 279 374 which relates to a process for the production of a catalyst containing Mo, Fe, Bi which is characterized by its specific surface, pore volume and pore distribution. On account of the production process, however, it is only possible to obtain catalyst particles substantially spherical in shape, i.e. with a very small ratio of surface to volume, or the particles would have to be very small. So far as industrial application is concerned, however, there are limits to this on account of the high pressure loss involved.

The catalysts produced and used by known methods have certain disadvantages in regard to the aspects mentioned. Elements of different shape are used with a view to shortening the diffusion paths, avoiding local overheating or achieving better utilization of the catalyst volumes by a suitable inner structure of the catalyst. Hitherto, individual measures along these lines have resulted in comparatively unsatisfactory productivity per catalyst volume used where catalysts of the type in question are used in the industrial production of acrolein. This is a considerable economic disadvantage because, by way of compensation, large and expensive reactors with a high filling volume for the catalysts have to be used to carry out the reaction.

One of the objects of the present invention was to provide an improved process for the production of acrolein by catalytic gas-phase oxidation of propene with air which would operate in known manner in the presence of steam and an inert gas or, preferably, waste gas from the reaction from which the condensible constituents have been removed, would use higher temperatures and in which the ratio of propene to air to inert gas or waste gas and water was 1:6–9:3–12:0–5.

BRIEF DESCRIPTION OF THE DRAWINGS

FIGS. 1 and 2 show examples of preferred shapes of the body of the catalyst.

DETAILED DESCRIPTION OF THE INVENTION

Figure 1:
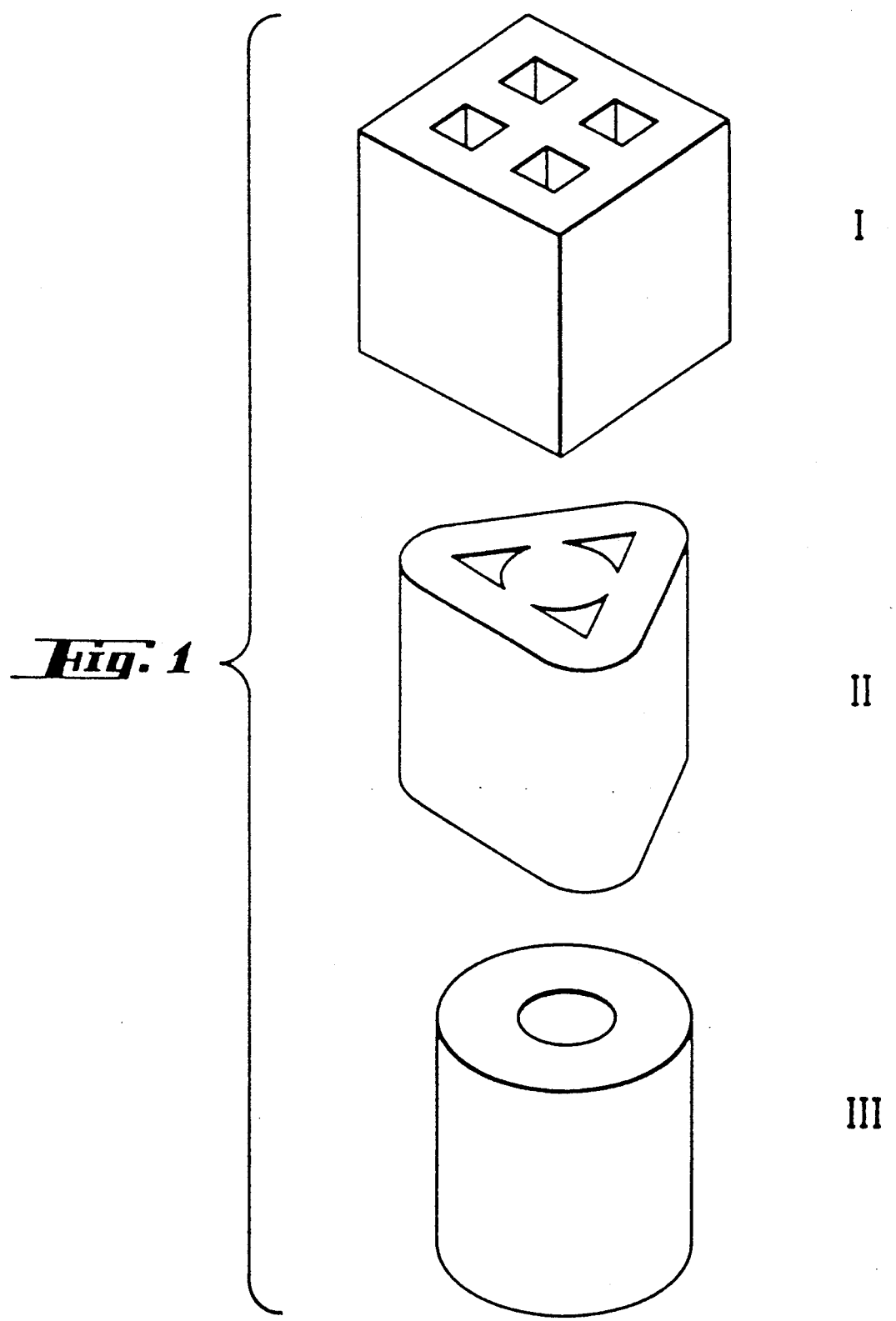

The above described object of the present invention was achieved when it was found that by using a catalyst which has an optimized chemical composition and which, through a new production process, has a particularly favorable outer form and internal structure and by applying a special temperature range and a slight excess pressure, it is possible to operate at very high specific loads without any loss of selectivity. The catalyst and its production are claimed in German patent application P 39 30 533.3 (89 177 Ky) which was filed at the same time as the present application.

More particularly, the process according to the present invention is characterized in that the gaseous starting materials are passed at 300° to 380° C. under an absolute pressure of 1.4 to 2.2 bar over a catalyst mass having the composition

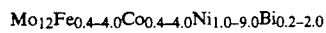
$Mo_{12}Fe_{0.4-4.0}Co_{0.4-4.0}Ni_{1.0-9.0}Bi_{0.2-2.0}$

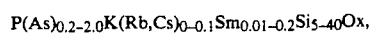
$P(As)_{0.2-2.0}K(Rb,Cs)_{0-0.1}Sm_{0.01-0.2}Si_{5-40}O_x,$ the element silicon being present in the form of pyrogenic or highly disperse precipitated silica, silica sol, finely divided aluminum silicate and, more particularly, in the form of montmorillonite and the catalyst mass in the form of a bed of individual catalyst elements having the following properties in combination:

a) catalyst elements of any geometric shape in which the ratio of outer surface Op to volume Vp is above 1.6 mm$^{-1}$ and of which the spatial dimension, defined by the diameter of a sphere which still just surrounds it, is smaller than 7.5 mm;

b) a porosity of the catalyst of at least 0.46, the absence of micropores (<2 nm), a mesopore volume (2–30 nm) of at least 0.03 cm$^3$/g, and a macropore volume (>30 nm) of at least 0.30 cm$^3$/g;

c) a mercury density of the catalyst element of at least 1.25 g/cm$^3$;

d) a specific BET surface of at least 10 m$^2$/g;

e) a breaking strength of at least 6.0 N;

f) an abrasion of less than 50 mg/g catalyst;

g) a pressure loss of less than 1,600 Pa/m of a catalyst bed introduced into a 2 cm diameter tube, and a specific load of 2–8 mol propene/dm$^3$ catalyst bed/h being adjusted.

The catalyst used in the process according to the present invention affords major advantages in regard to volume-time yield in all the mixed oxide formulations proposed for the gas-phase oxidation of propene. The activity required for a high volume/time yield is made possible by the favorable ratio between outer surface and volume and the favorable inner structure. By virtue of the increased ratio of surface to volume, the particular catalytically active mass is readily accessible to the reactants and the diffusion paths are short. The result of the favorable inner structure is that the resistance to diffusion within the catalyst is minimal. The high activity attributable to the large inner surface may thus be effectively utilized. Basically, the reduced resistance to diffusion in the catalyst element also has a favorable effect on selectivity.

The body of the catalyst according to the invention may have any geometric shape. Examples of preferred shapes are shown in the accompanying drawings (FIGS. 1 and 2).

A preferred variant of the catalyst formulation for the process consists of a mass having the following composition:

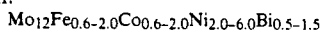

$Mo_{12}Fe_{0.6-2.0}Co_{0.6-2.0}Ni_{2.0-6.0}Bi_{0.5-1.5}$

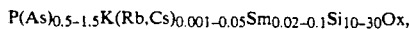

$P(As)_{0.5-1.5}K(Rb,Cs)_{0.001-0.05}Sm_{0.02-0.1}Si_{10-30}O_x,$ the element silicon being present in the form of pyrogenic SiO$_2$ and montmorillonite in a ratio by weight of 1:0.5 to 1:4. It has proved to be appropriate in this regard for the montmorillonite to have a specific BET surface reduced by calcination of less than 2.0 m$^2$/g.

In a particularly advantageous embodiment, the reaction is carried out in tube bundle reactors of which the tubes have an internal diameter of 16 to 25 mm.

The catalysts to be used in the process according to the present invention may be obtained as follows:

a) a suspension of the co-precipitate obtained in known manner by combining salt solutions of the catalytically active elements (except Si) is mixed with the insoluble silicon-containing solid and the suspension obtained is spray-dried under conditions which provide for an initial temperature of the drying air of 300° C. to 600° C., a temperature during deposition of the dried powder of 120° C. to 220° C. and a spraying intensity designed to produce a spray-dried powder having an average particle diameter of less than 30 μm, the residence time of the spray-dried powder in the dryer being from 2 to 25 seconds, b) the spray-dried powder is calcined in a furnace, preferably a rotary kiln, over residence times of 5 to 60 minutes and at a peak temperature in the spray-dried powder of 320° to 480° C., c) the calcined spray-dried powder is extruded with 5 to 40% by weight, based on the quantity of spray-dried powder, of a pore-forming agent which decomposes completely at a temperature below 400° C. and with wetting agents, lubricants and binders in a quantity sufficient to produce an extrudable mass, the wetting agents, lubricants and binders together making up no more than 40% by weight of the quantity of spray-dried powder, in the required geometric shape at a temperature below 80° C. and under a pressure blow 50 bar and the extruded strand is divided up by cutting to the length of the desired element.

d) the extruded individual elements are dried, the decomposable substance present is carefully removed by burning out in a furnace, preferably a rotary kiln, and the individual elements are conditioned in an air stream for 5 to 60 minutes at a peak temperature, as measured in the bed of individual elements, of 450° to 650° C.

This catalyst production process is based on a procedure which comprises a combination of spray drying of the starting material under defined conditions, intermediate conditioning within the stated temperature range, extrusion of the calcined spray-dried power with defined quantities of a pore-forming agent and typical processing aids in limited quantities by weight under exact extrusion conditions and final conditioning in air at a raised temperature level. In one favorable embodiment of the process according to the present invention, solid pentaerythritol having an average particle diameter of less 40 μm is used as the pore-forming agent. In addition to pentaerythritol cellulose powder, urea, oxalic acid and polyvinyl alcohol may be used as the pore-forming agent.

Spray drying of the suspension of the co-precipitate under the stated conditions results in the formation of spherical spray-dried particles of high inner porosity. The high inner surface required for such catalysts is produced in this way. The intermediate conditioning step removes all decomposable constituents from the primary particles so that no reduction in strength can occur during the final conditioning step.

Under the effect of the pore-forming agent added during the extrusion step, preferably in the same particle size range as the primary particles, a macropore system is formed during the final conditioning step, making the highly reactive mesoporous primary particles readily accessible to the reactants. Petroleum or water may advantageously be used as lubricant during the extrusion step while a 1 to 10% by weight aqueous methyl cellulose solution, preferably in the form of an oil-in-water emulsion, may advantageously be used as wetting agent and binder or lubricant or dry methyl cellulose powder may advantageously be used as binder.

The final conditioning step at 450° to 650° C. includes preliminary careful burning out during heating. However, the burning out and conditioning of the extruded individual elements may also be carried out in separate steps. In both cases, particularly good results are obtained if the extruded individual elements and the air stream are moved in co-current during the burning out phase and if the burning out phase is carried out at a temperature of at most 400° C.

Where the catalysts mentioned are used for the oxidation of propene to acrolein with air, the very favorable operating conditions claimed, which lead to high productivity, must be applied.

EXAMPLES

The invention is illustrated in the following by Examples in conjunction with the accompanying drawings where the Figures show preferred geometric forms for the catalyst elements:

The variables cited in the Examples are determined as follows:

1) Determination of porosity:
   Porosity is calculated from the mercury and helium density in accordance with the following equation:

porosity=(1—Hg density/He density). 100
   (dimensionless)

"Porosity" is the percentage empty volume of the catalyst mass in relation to its overall volume.

2) Determination of mesopore volume:
   Barrett, E. P.; Joyner, L. G.; and Halenda, P. P., J. Am. Chem. Soc., 73 (1951), page 373.

3) Determination of macropore volume:
   Hg injection process using a Carlo-Erba 200 porosimeter up to 1,000 bar pressure.

4) Determination of bulk density, mercury density (apparent density) and helium density (true density):
   Bulk density is determined by uniformly filling a straight steel tube having an internal diameter of 20 mm with 200 g catalyst in 1 minute and measuring the height of the resulting catalyst bed. Mercury density is determined by introducing 2 g of the catalyst size-reduced to 200 μm into a pycnometer with a volume of 25 ml and then carefully filling the pycnometer with mercury. The mercury density (or apparent density) of the catalyst is obtained from the mass of the mercury required to fill the pycnometer with and without the catalyst sample and the mass of the catalyst sample itself. The helium density (or true density) of the catalyst mass is determined with a Beckmann air reference pycnometer.

5) Determination of BET surface in accordance with DIn 66 131 (measuring gas $N_2$):
   Heating conditions: dried for 15 h at 100° C., degassed in vacuo for 1 h at 200° C.

6) Determination of breaking strength:
   Breaking strength is measured perpendicularly to the extrusion direction using an Erweka TBA 28, arithmetic mean of 100 individual measurements +/− standard deviation.

7) Determination of abrasion:
   Abrasion is measured with a Roche TA3-R Friabilator, sample weight 50 g, 10 r.p.m., load application time 5 mins.; result expressed as abrasion of catalyst particles <1 mm in mg/g catalyst.

8) Determination of pressure loss:
   Catalyst is uniformly introduced for 1 minute into a tube having an internal diameter of 2 cm, which is closed at its lower end by a wire gauze, in such a quantity that the height of the catalyst bed is 1 m. Air at 20° C. is then passed through the catalyst bed at a rate of 1 $Nm^3$/h and the pressure loss is measured.

9) Determination of particle size distribution:
   Particle size distribution is measured with a CILAS 715 granulometer. Ethanol is used as the suspension liquid. To destroy agglomerates, ultrasound is applied for 1 minute.

10) Determination of catalytic properties:
    The catalytic effect of the finished catalysts is tested in the reaction of propene to acrolein in an industrial tube reactor with an internal diameter of 20.5 mm externally cooled by a salt bath(length of catalyst bed 250 cm). The reaction is carried out with an input of 5.8 mol propene/h (or 5.2 mol propene/h, marked with an asterisk in Table 3), 43.5 mol air/h, 34.8 mol waste gas (composition: 5% $O_2$, 1% propene, 94% inert gas ($CO_2$, CO, $N_2$, Ar, propane)) and 2.9 mol $H_2O$/h and under a pressure of 1.8 bar at the entrance to the catalyst bed. The salt bath temperature adjusted, the maximum over-temperature obtained (exotherms) in the middle of the tube and the measured conversions and yields are shown in Table 3.

The acrolein yield (%) is defined as
$$\frac{\text{mol/h acrolein formed}}{\text{mol/h propene introduced}} \cdot 100$$

The acrylic acid yield (%) is defined as
$$\frac{\text{mol/h acrylic acid formed}}{\text{mol/h propene introduced}} \cdot 100$$

The conversion of propene (%) is defined as
$$1 - \frac{\text{mol/h propene issuing from the reaction tube}}{\text{mol/h propene introduced into the reaction tube}} \cdot 100$$

The acrolein selectivity (%) is defined as
$$\frac{\text{acrolein yield}}{\text{propene conversion}} \cdot 100$$

The acrylic acid selectivity (%) is defined as
$$\frac{\text{acrylic acid yield}}{\text{propene conversion}} \cdot 100$$

The acrolein productivity is defined as
$$\frac{\text{g/h acrolein formed}}{\text{dm}^3 \text{ catalyst bed}}$$

The following Examples relate to the production and use of the catalysts listed in Table 1.

EXAMPLE 1

The catalyst composition shown under Example No. 1 in Table 1 was produced as follows in geometric form III of FIG. 1:

The co-precipitate for the production of the active catalyst phase is obtained by dissolving 484.8 g Fe(-$NO_3)_3$.9 $H_2O$, 291.0 g Co($NO_3)_2$.6 $H_2O$, 1,163.2 g Ni(-$NO_3)_2$.6 $H_2O$ and 2.5 g $KNO_3$ in 3.1 l water and adding a solution of 17.4 g $Sm_2O_3$ in 106 g conc. $HNO_3$ with stirring at 90° C. 601 g highly disperse silica (Aerosil 200) and 1,202 g conditioned montmorillonite (specific BET surface <1 $m^2$/g) are added to the resulting solution with continued stirring.

A solution of 2,118.6 g $(NH_4)_6MO_7O_{24}6H_2O$ in 2.7 l $H_2O$ is prepared in a separate vessel at 60° C. and 92.2 g 85% $H_3PO_4$ are added with intensive stirring to the solution thus prepared.

The two solutions are then combined with intensive stirring and a solution of 242.5 g Bi($NO_3)_3$.5$H_2O$ in 204 g 8.2% $HNO_3$ is added to the combined solutions. The suspension obtained is dried in a spray dryer at an entry temperature of the drying air of 550° C. The ratio of the quantity of drying air to the quantity of suspension sprayed is adjusted to give an exit temperature of 170° C. and the quantity of suspension is gauged to give a residence time of 6 seconds of the spray-dried powder in the spray dryer. The spraying intensity is selected so that a spray dried powder having an average particle diameter dp of 25 μm is obtained. The spray-dried powder is calcined in a rotary kiln for 30 minutes at a maximum temperature in the spray dried powder of 420° C.

1.6 kg of the calcined spray-dried powder are introduced into a combined kneader/extruder and mixed for 5 minutes with 0.4 kg pentaerythritol ("very finely ground") having an average particle diameter dp of 40 μm. 493 g of a 6% by weight tylose solution in which 26.6 g petroleum have been emulsified are then added to the resulting mixture. The mass is then kneaded until a homogeneous plastic state is reached. The plastic mass is then extruded under a pressure of 10 bar and at a temperature in the extruded mass of 30° C. The extruded hollow strand is cut at 5 mm intervals and the rings obtained (diameter 5 mm, length 5 mm, internal diameter 1.8 mm) are carefully dried at 80° C.

The dried rings are introduced into a heated rotary kiln and are heated at a rotational speed of 2 min$^{-1}$ in the presence of excess air to a peak temperature of 600° C. in the bed passing through the rotary kiln. The residence time in the rotary kiln is 30 minutes.

The physical properties of the catalyst composition and its intermediate stages are shown in Table 2 while the effect of the catalyst in the production of acrolein is shown in Table 3.

EXAMPLE 2

In Example 2, the same catalyst composition as in Example 1 was produced in geometric form VI of FIG. 2.

As in Example 1, the co-precipitate of the active catalyst phase is produced, dried, calcined and kneaded in a combined kneader/extruder until a homogeneous plastic state is reached. The plastic mass is extruded under a pressure of 15 bar and at a temperature of 32° C. in the extruded mass. The hollow strand extruded in form VI of FIG. 2 is cut at 5 mm intervals and the catalyst blanks thus obtained are dried and conditioned in a rotary kiln as in Example 1.

EXAMPLE 3

In Example 3, the same catalyst composition as in Example 1 was produced in geometric form II of FIG. 1.

As in Example 1, the co-precipitate of the active catalyst phase is produced, dried, calcined and kneaded in a combined kneader/extruder until a homogeneous plastic state is reached. The plastic mass is extruded under a pressure of 15 bar and at a temperature of 32° C. in the extruded mass. The hollow strand extruded in form II of FIG. 1 is cut at 5 mm intervals and the catalyst blanks thus obtained are dried and conditioned in a rotary kiln as in Example 1.

COMPARISON EXAMPLE 1

In Comparison Example 1, the same catalyst composition as in Example 1 was extruded in the form of strands.

As in Example 1, the co-precipitate of the active catalyst phase is produced, dried, calcined and kneaded in a combined kneader/extruder until a homogeneous plastic state is reached. The plastic mass is extruded under a pressure of 8 bar and at a temperature of 25° C. in the extruded mass. The catalyst mass extruded in form of a solid strand 5 mm in diameter is cut at 5 mm intervals and the catalyst blanks thus obtained are dried and conditioned in a rotary kiln as in Example 1.

In Examples 4, 5 and 6 below, various catalyst compositions are produced in geometric form III of FIG. 1 as in Example 1.

EXAMPLE 4

The co-precipitate for the production of the active catalyst phase is obtained by dissolving 242.4 g Fe(NO$_3$)$_3$.9 H$_2$O, 232.8 g Co(NO$_3$)$_2$.6 H$_2$O, 1,744.8 g Ni(NO$_3$)$_2$.6H$_2$O and 5.1 g KNO$_3$ in 3.1 l water and adding a solution of 34.9 g Sm$_2$O$_3$ in 212 g conc. HNO$_3$ with stirring at 90° C. 300.5 g highly disperse silica (Aerosil 200) and 300.5 g conditioned montmorillonite (specific BET surface <1 m$^2$/g) are added to the resulting solution with continued stirring. A solution of 2,118.6 g (NH$_4$)$_6$Mo$_7$O$_{24}$.6H$_2$O in 2.7 l H$_2$O is prepared in a separate vessel at 60° C. and 115.3 g 85% H$_3$PO$_4$ are added with intensive stirring to the solution thus prepared. The two solutions are then combined with intensive stirring and a solution of 485.1 g Bi(NO$_3$)$_3$.5H$_2$O in 408 g 8.2% HNO$_3$ is added to the combined solutions. The suspension obtained is dried in a spray dryer at an entry temperature of the drying air of 550° C. The ratio of the quantity of drying air to the quantity of suspension sprayed is adjusted to give an exit temperature of 170° C. while the quantity of suspension is gauged to give a residence time of 6 seconds of the spray-dried powder in the spray dryer. The spraying intensity is selected so that a spray dried powder having an average particle diameter dp of 25 μm is obtained. The spray-dried powder is calcined in a rotary kiln for 30 minutes at a maximum temperature in the spray dried powder of 420° C.

The calcined spray-dried powder is further processed as in Example 1, except for the fact that the extruded hollow strand has an internal diameter of 2 mm.

EXAMPLE 5

The co-precipitate for the production of the active catalyst phase is obtained by dissolving 808.0 g Fe(NO$_3$)$_3$.9 H$_2$O, 320.1 g Co(NO$_3$)$_2$.6 H$_2$O, 1,744.8 g Ni(NO$_3$)$_2$.6H$_2$O and 0.1 g KNO$_3$ in 3.1 l water and adding a solution of 34.9 g Sm$_2$O$_3$ in 212 g conc. HNO$_3$ with stirring at 90° C. 600.9 g highly disperse silica (Aerosil 200) and 1,201.8 g conditioned montmorillonite (specific BET surface <1 m$^2$/g) are added to the resulting solution with continued stirring. A solution of 2,118.6 g (NH$_4$)$_6$Mo$_7$O$_{24}$.6H$_2$O in 2.7 l H$_2$O is prepared in a separate vessel at 60° C. and 115.3 g 85% H$_3$PO$_4$ are added with intensive stirring to the solution thus prepared. The two solutions are then combined with intensive stirring and a solution of 485.1 g Bi(NO$_3$)$_3$.5H$_2$O in 408 g 8.2% HNO$_3$ is added to the combined solutions. The suspension obtained is dried in a spray dryer at an entry temperature of the drying air of 550° C. The ratio of the quantity of drying air to the quantity of suspension sprayed is adjusted to give an exit temperature of 170° C. while the quantity of suspension is gauged to give a residence time of 6 seconds of the spray-dried powder in the spray dryer. The spraying intensity is selected so that a spray dried powder having an average particle diameter dp of 25 μm is obtained. The spray-dried powder is calcined in a rotary kiln for 30 minutes at a maximum temperature in the spray dried powder of 420° C.

The calcined spray-dried powder is further processed as in Example 4.

EXAMPLE 6

The co-precipitate for the production of the active catalyst phase is obtained by dissolving 646.4 g Fe($NO_3$)$_3$.9$H_2O$, 174.6 g Co($NO_3$)$_2$.6$H_2O$, 1,744.8 g Ni($NO_3$)$_2$.6$H_2O$ and 0.1 g $KNO_3$ in 3.1 l water and adding a solution of 34.9 g $Sm_2O_3$ in 212 g conc. $HNO_3$ with stirring at 90° C. 600.9 g highly disperse silica (Aerosil 200) and 1,201.8 g conditioned montmorillonite (specific BET surface <1 $m^2$/g) are added to the resulting solution with continued stirring. A solution of 2,118.6 g ($NH_4$)$_6$$Mo_7$$O_{24}$.6$H_2O$ in 2.7 l $H_2O$ is prepared in a separate vessel at 60° C. and 115.3 g 85% $H_3PO_4$ are added with intensive stirring to the solution thus prepared. The two solutions are then combined with intensive stirring and a solution of 727.7 g Bi($NO_3$)$_3$.5$H_2O$ in 612.0 g 8.2% $HNO_3$ is added to the combined solutions. The suspension obtained is dried in a spray dryer at an entry temperature of the drying air of 550° C. The ratio of the quantity of drying air to the quantity of suspension sprayed is adjusted to give an exit temperature of 170° C. while the quantity of suspension is gauged to give a residence time of 6 seconds of the spray-dried powder in the spray dryer. The spraying intensity is selected so that a spray-dried powder having an average particle diameter dp of 25 μm is obtained. The spray-dried powder is calcined in a rotary kiln for 30 minutes at a maximum temperature in the spray-dried powder of 420° C.

The calcined spray-dried powder is further processed as in Example 4.

EXAMPLE 7

The same catalyst composition as in Example 1 is shaped in Example 7, except for the fact that, in Example 7, pentaerythritol is replaced by cellulose powder as the pore-forming agent.

The calcined spray-dried powder is produced as in Example 1.

1.6 kg of the calcined spray-dried powder are introduced into a combined kneader/extruder and mixed for 5 minutes with 0.4 kg cellulose powder, average particle diameter dp=36 μm, as pore-forming agent.

The mixture is further processed as in Example 1.

COMPARISON EXAMPLE 2

In Comparison Example 2, the catalyst is produced in the same way as in Example 1, except that no pore-forming agent is added during the shaping process.

The calcined spray-dried powder is produced in the same way as in Example 1.

1.6 kg of the calcined spray-dried powder are introduced into a combined kneader/extruder. 394.4 g of a 6% by weight tylose solution in which 21.3 g petroleum have been emulsified are then added. The mass is kneaded until a homogeneous plastic state is reached. The plastic mass obtained is extruded in form III of FIG. 1 under a pressure of 14 bar and at a temperature of 32° C. in the extruded mass.

The extruded mass is further processed in the same way as in Example 1, except that the peak temperature during conditioning in the rotary kiln is increased to 620° C.

German Patent Application P 39 30 534.1 is hereby incorporated by reference.

It will be appreciated that the instant specification and claims are set forth by way of illustration and not limitation and that various modifications and changes may be made without departing from the spirit and scope of the present invention.

TABLE 1

| | | CATALYST COMPOSITION (ATOMIC NUMBERS) | | | | | | | | |
|---|---|---|---|---|---|---|---|---|---|---|
| Examples | Comp. Ex. | Mo | Fe | Co | Ni | Bi | P | K | Sm | Si (as montmorillonite + high disp. silica) |
| 1, 2, 3, 7 | 1, 2 | 12 | 1.2 | 1.0 | 4.0 | 0.5 | 0.8 | 0.025 | 0.1 | 30 |
| 5 | | 12 | 0.6 | 0.8 | 6.0 | 1.0 | 1.0 | 0.05 | 0.2 | 10 |
| 6 | | 12 | 2.0 | 1.1 | 6.0 | 1.0 | 1.0 | 0.001 | 0.2 | 30 |
| 7 | | 12 | 1.6 | 0.6 | 6.0 | 1.5 | 1.0 | 0.001 | 0.2 | 30 |

TABLE 2

| | | | | | | | | | | | | | |
|---|---|---|---|---|---|---|---|---|---|---|---|---|---|
| Ex. | Comp. Ex. | $O_p/V_p$ $mm^{-1}$ | $d_K$* | Porosity | $V_{meso}$ ml/g | $V_{macro}$ ml/g | Bulk g/ml | He— g/ml | Hg density g/ml | BET surf. $m^2$/g | Breaking strength N | Abrasion mg/g | Δ p Pa/m |
| 1 | | 1.65 | 7.1 | 0.51 | 0.05 | 0.38 | 0.76 | 3.48 | 1.71 | 14 | 14.9 | 16 | 1450 |
| 2 | | 2.00 | 7.1 | 0.62 | 0.05 | 0.48 | 0.60 | 3.49 | 1.30 | 16 | 9.8 | 32 | 1400 |
| 3 | | 2.10 | 7.1 | 0.62 | 0.04 | 0.42 | 0.70 | 2.54 | 1.30 | 16 | 15.4 | 48 | 1340 |
| | 1 | 1.2 | 7.1 | 0.64 | 0.04 | 0.42 | 0.79 | 3.59 | 1.30 | 16 | 18.9 | 20 | 1520 |
| 4 | | 1.73 | 7.1 | 0.56 | 0.03 | 0.39 | 0.70 | 4.02 | 1.77 | 12 | 6.2 | 8 | 1260 |
| 5 | | 1.73 | 7.1 | 0.56 | 0.04 | 0.30 | 0.72 | 4.05 | 1.79 | 11 | 10.7 | 4 | 1190 |
| 6 | | 1.73 | 7.1 | 0.56 | 0.03 | 0.29 | 0.73 | 4.08 | 1.81 | 12 | 7.7 | 14 | 1290 |
| 7 | | 1.65 | 7.1 | 0.62 | 0.04 | 0.33 | 0.76 | 3.51 | 1.30 | 16 | 14.4 | 18 | 1430 |
| | 2 | 1.65 | 7.1 | 0.44 | 0.05 | 0.25 | 0.87 | 3.46 | 1.93 | 13 | 16.8 | 11 | 1400 |

*$d_K$ = diameter of the sphere in which the catalyst can still just fit

TABLE 3

Effect of the catalysts in the production of acrolein

| Ex. | Comp. Ex. | Salt bath temp. °C. | Conversion % | Exotherms ° | Acrol. yield % | Acrylic acid Yield % | Acrol. select % | Acrylic acid select. % | Productivity g acrol./dm³ catal./h |
|---|---|---|---|---|---|---|---|---|---|
| 1 |   | 331 | 94.2 | 81 | 81.8 | 7.0 | 86.8 | 7.4 | 322 |
| 2 |   | 347 | 93.4 | 78 | 81.4 | 7.3 | 87.1 | 7.8 | 320 |
| 3 |   | 345 | 92.7 | 76 | 80.9 | 7.1 | 87.2 | 7.7 | 318 |
|   | 1 | 330 | 93.1 | 78 | 77.6 | 8.5 | 83.3 | 9.1 | 273* |
| 4 |   | 364 | 91.1 | 72 | 80.3 | 8.7 | 88.1 | 9.5 | 316 |
| 5 |   | 344 | 90.9 | 76 | 80.1 | 9.0 | 88.1 | 9.9 | 315 |
| 6 |   | 359 | 91.3 | 72 | 80.3 | 8.8 | 87.9 | 9.6 | 316 |
| 7 |   | 348 | 92.6 | 77 | 80.4 | 6.9 | 86.8 | 7.5 | 317 |
|   | 3 | 350 | 90.0 | 74 | 77.1 | 6.0 | 85.6 | 6.7 | 272* |

*Input 5.2 mol propene/h

What is claimed:

1. A process for the production of acrolein by catalytic gas-phase oxidation of propene with air in the presence of steam and an inert gas or waste gas from said reaction from which the condensible constituents have been removed, at elevated temperature and in a ratio of propene to air to inert gas or waste gas to water of 1:6–9:3–12:0–5, comprising passing said gaseous starting materials at 300° to 380° C. under an absolute pressure of 1.4 to 2.2 bar over a catalyst mass having the composition $$Mo_{12}Fe_{0.4-4.0}Co_{0.4-4.0}Ni_{1.0-9.0}Bi_{0.2-2.0}$$

$$P(As)_{0.2-2.0}K(Rb,Cs)_{0-0.1}Sm_{0.01-0.2}Si_{5-40}O_x,$$

the element silicon being at least one member selected from the group consisting of pyrogenic or highly disperse precipitated silica, silica sol, finely divided aluminum silicate, and montmorillonite, and the catalyst mass is in the form of a bed of individual catalyst elements having the following properties in combination:

a) catalyst elements of any geometric shape in which the ratio of outer surface Op to volume Vp is above 1.6 mm$^{-1}$ and of which the spatial dimension, defined by the diameter of a sphere which still just surrounds it, is smaller than 7.5 mm;

b) a porosity of the catalyst of at least 0.46, the absence of micropores (<2 nm), a mesopore volume (2–30 nm) of at least 0.03 cm³/g and a macropore volume (>30 nm) of at least 0.30 cm³/g;

c) a mercury density of the catalyst element of at least 1.25 g/cm³;

d) a specific BET surface of at least 10 m²/g;

e) a breaking strength of at least 6.0 N;

f) an abrasion of less than 50 mg/g catalyst;

g) a pressure loss of less than 1,600 Pa/m of a catalyst bed introduced into a 2 cm diameter tube, and a specific load of 2–8 mol propene/dm³ catalyst bed/h being adjusted.

2. The process according to claim 1 wherein said catalyst mass has the following composition:

$$Mo_{12}Fe_{0.6-2.0}Co_{0.6-2.0}Ni_{2.0-6.0}Bi_{0.5-1.5}$$

$$P(As)_{0.5-1.5}K(Rb,Cs)_{0.001-0.05}Sm_{0.02-0.1}Si_{10-30}O_x,$$

the element silicon being present in the form of pyrogenic $SiO_2$ and montmorillonite in a ratio by weight of 1:0.5 to 1:4.

3. The process according to claim 2 wherein said montmorillonite has a specific BET surface reduced by calcination of less than 2.0 m²/g.

4. The process according to claim 1 wherein said reaction is carried out in tube bundle reactors of which the tubes have an internal diameter of 16 to 25 mm.

5. The process according to claim 1 wherein said silicon is montmorillonite.

6. The process according to claim 1, wherein said waste gas from said reaction, from which the condensible constituents have been removed, is present.

* * * * *